United States Patent [19]

Jensen

[11] 4,379,140

[45] Apr. 5, 1983

[54] TURKEY RHINOTRACHEITIS VACCINE

[75] Inventor: Marcus M. Jensen, Provo, Utah

[73] Assignee: Brigham Young University, Provo, Utah

[21] Appl. No.: 224,402

[22] Filed: Jan. 12, 1981

[51] Int. Cl.³ .......................... A61K 39/02; C12N 1/20
[52] U.S. Cl. ......................................... 424/92; 424/93; 435/253
[58] Field of Search .................... 424/92, 93; 435/172, 435/253

[56] References Cited

PUBLICATIONS

D. G. Simmons, et al., Avian Diseases, vol. 24, pp. 82–90 (1980).
D. G. Simmons, et al., Avian Diseases, vol. 23, pp. 194–203 (1979).
T. Shimizu, Infec. Immun, vol. 22, pp. 318–321 (1978).
I. Hertman, et al., Avian Diseases, vol. 23, pp. 863–885 (1979).
Lamanna, C. and Mallette, M., Basic Bacteriology, pp. 723–727, Williams & Wilkins Co., publisher, Baltimore, 1965.
Metzler, D., Biochemistry-The Chemical Reactions of Living Cells, pp. 945–946, Academic Press, New York, 1977.
Michael, A., et al., Avian Diseases, vol. 24, pp. 870–885, 1979.

*Primary Examiner*—Blondel Hazel
*Attorney, Agent, or Firm*—Paul H. Ginsburg; Bruce M. Eisen

[57] ABSTRACT

A live vaccine against *Alcaligenes faecalis*, for application to turkeys, containing a temperature-sensitive non-virulent genetically stable strain of *Alcaligenes faecalis* having good immunizing capabilities and the absence of adverse side-effects.

8 Claims, No Drawings

TURKEY RHINOTRACHEITIS VACCINE

The present invention relates to a turkey rhinotracheitis vaccine.

Turkey rhinotracheitis, also referred to as turkey coryza, is an acute upper respiratory disease of turkeys which is caused by the bacterium *Alcaligenes faecalis. A. faecalis* invades the upper respiratory tract causing excessive accumulation of mucus and minor lesions in the epithelial tissues of the nasal cavity and trachea. The most characteristic lesions are mucoid rhinotracheitis accompanied by structural collapse of the trachea.

The first sign of coughing generally occurs in infected turkeys from seven days to twenty weeks of age. This may be accompanied by a mucoid discharge from the nose and eyes. These signs may progress into severe rhinitis with coughing, moist rales, and depression.

Although the incidence of coryza is high among birds raised in confinement, mortality is usually low, unless accompanied by secondary infections, e.g. *P. multocida* or certain *E. coli* strains, or other complications. Mortality will peak at seven to fourteen days after onset of clinical signs and if complications do not occur, it will remain below 10 to 15% of the turkeys. When coryza is compounded with concurrent stress such as dust, crowding, heat, chilling, vaccinations, or other infections, death rates may exceed 50%.

Until the development of the present vaccine, no other vaccine has been available that was effective in preventing rhinotracheitis in turkeys. Killed vaccines had been tried, but were not effective. Also unsuccessful, were attempts to select naturally occuring mutants that might work as vaccines.

The present invention relates to novel live vaccines for the vaccination of turkeys against *A. faecalis* which comprise temperature sensitive avirulent stable strains of *A. faecalis*. These temperature sensitive strains exhibit reduced growth or no growth at 42° C. but grow well at about 30° to 34° C. The present invention also relates to a process for preparing such non-virulent strains which can be used as active ingredients in vaccines. The present invention further relates to such temperatures sensitive strains.

A preferred embodiment of the present invention comprises a novel temperature-sensitive mutant strain of *A. faecalis*, designated mutant strain 87, which has been deposited with the American Type Culture Collection of Rockville, Md. and has been assigned ATCC No. 31770. This strain exhibits reduced growth at 42° C. but grows well at 30° to 34° C., thus permitting colonization of only the nasal and upper tracheal mucosa of turkeys. Bacteria invading the lower trachea and lungs will not multiply or persist at the internal body temperature (41°–42° C.) of turkeys. Vaccination with the mutant strain of the present invention results in colonization of the nasal and upper tracheal mucosa and produces a strong immune response that correlates with the appearance of circulating antibodies. The unique characteristics of the strain of the present invention result in a vaccine that is devoid of any detectable adverse side-effects, while providing a significant immunity to rhinotracheitis.

From current evidence, it appears that all *A. faecalis* isolates causing rhinotracheitis in turkeys are of the same serotype. Thus, the vaccine of the present invention should offer protection against rhinotracheitis in most turkeys.

The vaccine of the present invention is preferably administered at a dose of about 50 to 200 million bacteria per bird, more preferably about 100 to 200 million bacteria. The vaccine is preferably administered at 2 to 3 weeks of age, and is preferably followed by re-vaccination at 4 to 6 weeks of age. When turkey poults are exposed to virulent strains of *A. faecalis* early in life, sometimes at one day of age, the vaccine of the present invention may be administered to poults on the first day of life. It is preferable to avoid administering any medication, particularly antibiotics, to the birds for 3 to 4 days before and after vaccination.

The preferred vaccine of the present invention may be administered by mixing the mutant strain 87 in the birds' drinking water and making such water available to the birds for 4 to 24 hours. The vaccine may also be administered intranasally by dropping in the naries or as an aerosol. The number of bacteria in drinking water should be about $10^5$ to $10^7$ per ml. For best results, turkeys should be deprived of water for 2 hours before administration of the vaccine.

The following non-limiting Examples are illustrative of the present invention:

EXAMPLE I

Preparation of Temperature Sensitive Mutant Strain

The preferred temperature-sensitive mutant strain of the invention was produced by a modification of the method of T. Shimizu, *Infec. Immun.*, 22:318–321 (1978), the disclosure of which is hereby incorporated herein by reference. A field culture of virulent *A. faecalis* obtained from a turkey with clinical rhinotracheitis was exposed to 350 ug/ml of the mutagen N-methyl-N'-nitro-N-nitrosoguanidine (NTG) while in the logarithmic phase of growth. After 30 minutes exposure to NTG, the bacteria was washed twice with phosphate buffered saline (PBS) at pH 7.2. About 1 to 2% of the bacteria survived the NTG treatment. The surviving bacteria was diluted and plated on tryptic soy agar (TSA) plates and incubated at 37° C. for 48 hours. Plates containing between 100 to 150 colonies were replicate plated onto three fresh TSA plates, one plate was incubated at 30° C., one at 37° C., and one at 42° C. A colony that developed at 30° C. and 37° C., but was absent at 42° C. was selected as the first-step temperature sensitive (ts) mutant. This first-step ts mutant was then treated with 400 ug/ml of NTG for 30 minutes and the survivors were plated and replicate plated as described above. From these plates, a colony was selected that grew as well as the first-step ts-mutant at 30° C., but produced a smaller colony than the first-step ts mutant at 37° C., and produced no colony in 24 hours at 42° C. Bacteria from this colony were second-step ts-mutants and were designated strain 87 and have been deposited as ATTC No. 31770. Six other ts-mutants were produced by exposure to NTG, but none of these possessed the ideal combination of good immunizing capabilities and absence of adverse side-effects that were seen with strain 87. Strain 87 has been back passed 6 times in the nasal mucosa of turkeys and shows no signs of changes in growth characteristics or virulence and is thus considered to be genetically stable. The biochemical characteristics of strain 87 are the same as those reported from the wild isolate of *A. faecalis* by D. G. Simmons in *Avian Diseases*, vol. 24, page 82 (1980), the disclosure of which is hereby incorporated herein by reference.

EXAMPLE II

Vaccine Preparation

Several colonies of strain 87 were suspended in 3 ml of physiological saline solution which was then swabbed evenly over the surface of tryptic soy agar plates (Difco) with a sterile cotton swab. The plates were incubated for 36 hours at 30° C. The bacterial cells were harvested by flooding each plate with 10 ml of tryptic soy broth (Difco) and suspending the bacteria in the broth by rubbing the agar surface with a sterile cotton swab. The broth was removed with a pipette and vigorously pipetted in and out several times to produce an even suspension of cells. Plate counts were made from each pool of bacteria. The harvested bacteria was held at 4° C. in wet ice until administered as an oral vaccine later the same day. Such vaccine contains about $2 \times 10^{10}$ bacteria per ml. This vaccine will remain stable for 4 to 6 weeks when mixed with non-fat powdered milk (5 gm powder to 100 ml vaccine) and held at 4° C. Strain 87 is also stable for prolonged periods (many months) when lyophilized. The vaccine can also be produced by growing strain 87 in broth cultures for 36 to 48 hours at 30° C.

I claim:

1. A live vaccine against turkey rhinotracheitis having good immunizing capabilities and the absence of adverse side-effects, containing a pharmaceutically acceptable carrier and an immunologically effective amount of a temperature sensitive, non-virulent, genetically stable strain of *Alcaligenes faecalis* that can be back passed 6 times in the nasal mucosa of turkeys and show no signs of changes in growth characteristics or virulenece, said strain being substantially similar in immunizing properties to the strain of *Alcaligenes faecalis* ATCC No. 31770.

2. A live vaccine against turkey rhinotracheitis having good immunizing capabilities and the absence of adverse side-effects, containing a pharmaceutically acceptable carrier and an immunologically effective amount of a biologically pure culture of a temperature sensitive, non-virulent, genetically stable strain of *Alcaligenes faecalis* that can be back passed 6 times in the nasal mucosa of turkeys and show no signs of changes in growth characteristics or virulence, said strain being substantially similar in immunizing properties to the strain of *Alcaligenes faecalis* ATCC No. 31770.

3. A vaccine according to claim 1 or 2, in unit dosage form, containing about 50 to 200 million bacteria per bird dosage.

4. A method for the immunization of turkeys against rhinotracheitis which comprises applying the vaccine of claim 1 in an immunologically effective amount to a turkey.

5. A method according to claim 4, wherein said amount is about 50 to 200 million bacteria.

6. A method for the immunization of turkeys against rhinotracheitis which comprises applying the vaccine of claim 2 in an immunologically effective amount to a turkey.

7. A method according to claim 6, wherein said amount is about 50 to 200 million bacteria.

8. A biologically pure culture of a temperature sensitive, non-virulent, genetically stable strain of *Alcaligenes faecalis* which is the strain of *Alcaligenes faecalis* having ATCC No. 31770.

* * * * *